(12) United States Patent
Lee et al.

(10) Patent No.: US 9,061,137 B2
(45) Date of Patent: Jun. 23, 2015

(54) NERVE ELECTRODE PROVIDED WITH ANTI-INFLAMMATORY DRUG AND METHOD OF MANUFACTURING THE SAME

(71) Applicant: KOREA INSTITUTE OF SCIENCE AND TECHNOLOGY, Seoul (KR)

(72) Inventors: Soo Hyun Lee, Seoul (KR); Ji Yoon Kang, Seoul (KR); Nakwon Choi, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 13/688,729

(22) Filed: Nov. 29, 2012

(65) Prior Publication Data

US 2014/0100639 A1 Apr. 10, 2014

(30) Foreign Application Priority Data

Oct. 10, 2012 (KR) ........................ 10-2012-0112557

(51) Int. Cl.
*A61N 1/05* (2006.01)
*A61L 31/16* (2006.01)
(Continued)

(52) U.S. Cl.
CPC ............... *A61N 1/0553* (2013.01); *A61L 31/16* (2013.01); *A61N 1/0556* (2013.01); *A61B 2562/0209* (2013.01); *A61B 2562/125* (2013.01); *A61L 2400/12* (2013.01); *A61B 5/04001* (2013.01); *A61L 31/10* (2013.01); *A61L 2300/41* (2013.01);
(Continued)

(58) Field of Classification Search
CPC ......... A61N 1/04; A61N 1/05; A61N 1/0531; A61N 1/0543; A61N 1/0551; A61N 1/0553; A61N 1/0556

USPC .......... 607/2, 3, 116, 118, 120, 152; 600/372, 600/393
See application file for complete search history.

(56) References Cited

U.S. PATENT DOCUMENTS 3,654,933 A * 4/1972 Hagfors ........................ 607/118
5,265,608 A * 11/1993 Lee et al. ...................... 600/377
5,810,725 A * 9/1998 Sugihara et al. .............. 600/372
(Continued)

FOREIGN PATENT DOCUMENTS

| JP | 2008-54720 | 3/2008 |
| KR | 10-2009-0048600 | 5/2009 |
| KR | 10-2011-0084666 | 7/2011 |

OTHER PUBLICATIONS

Karen C. Cheung, "Implantable Microscale Neural Interfaces", Biomed Microdevices, 2007, vol. 9, pp. 923-938.
(Continued)

*Primary Examiner* — Carl H Layno
*Assistant Examiner* — Eugene Wu
(74) *Attorney, Agent, or Firm* — Goldilocks Zone IP Law

(57) ABSTRACT

A nerve electrode that is inserted into a living body and that is configured to attach to nerves is provided. The nerve electrode that is inserted into a living body and that is configured to attach to nerves includes: i) a flexible substrate; ii) a plurality of electrodes that are separately positioned on the flexible substrate; and iii) an insulating layer that is positioned at a separation space of the plurality of electrodes and that insulates the plurality of electrodes. The plurality of electrodes include i) at least one linear electrode, and ii) a planar electrode that is separated from the linear electrode. An anti-inflammatory drug transfer layer is positioned on the planar electrode.

9 Claims, 27 Drawing Sheets

(51) Int. Cl.
*A61L 31/10* (2006.01)
*A61B 5/04* (2006.01)

(52) U.S. Cl.
CPC .......... *A61L 2300/43* (2013.01); *A61L 2420/08* (2013.01)

(56) References Cited

U.S. PATENT DOCUMENTS

| 6,600,956 | B2* | 7/2003 | Maschino et al. ............ 607/118 |
| 7,815,615 | B2 | 10/2010 | Jolly et al. |
| 8,712,517 | B2 | 4/2014 | Jolly |
| 2002/0064546 | A1* | 5/2002 | Harris ............................ 424/426 |
| 2003/0187490 | A1* | 10/2003 | Gliner ............................ 607/116 |
| 2007/0060991 | A1* | 3/2007 | North et al. .................... 607/117 |
| 2007/0239245 | A1* | 10/2007 | Borgaonkar et al. ......... 607/121 |
| 2010/0057197 | A1* | 3/2010 | Weber et al. ................. 623/1.42 |
| 2011/0034857 | A1 | 2/2011 | Jolly et al. |

OTHER PUBLICATIONS

Patent Abstracts of Japan, Publication No. 2008-054720, published Mar. 13, 2008.
Korean Patent Abstracts, Publication No. 1020110084666, published Jul. 26, 2011.

* cited by examiner

NERVE ELECTRODE PROVIDED WITH ANTI-INFLAMMATORY DRUG AND METHOD OF MANUFACTURING THE SAME

CROSS-REFERENCE TO RELATED APPLICATION

This application claims priority to and the benefit of Korean Patent Application No. 10-2012-0112557 filed in the Korean Intellectual Property Office on Oct. 10, 2012, the entire contents of which are incorporated herein by reference.

BACKGROUND OF THE INVENTION (a) Field of the Invention

The present invention relates to a nerve electrode and a method of manufacturing the same. More particularly, the present invention relates to a nerve electrode and a method of manufacturing the same that suppress inflammation when inserting anti-inflammatory drugs into a living body while having the anti-inflammatory drugs.

(b) Description of the Related Art

For development of original technology for rehabilitation and welfare and practical use of the technology, a nerve stimulus apparatus using a nerve element facilitates improvement of quality of life of the soaring number of senior citizens as well as disabled people, and localizes rehabilitation and welfare related original devices through industrialization of related technology, and thus secures technical superiority in the world medical device market, and much research has thus been performed.

Implant type nerve electrode technology and medical treatment technology using the same is technology corresponding to an introduction time, and is expected to bring an economic/social/technical ripple effect through prior occupation of higher value-added original technology, as it contributes to improvement in quality of life of the socially disadvantaged such as senior citizens and disabled people. Presently used nerve devices include a heart pulsation stimulus device, a cerebral nerve stimulus device for Parkinson's disease, epilepsy, or chronic pain treatment, a central nerve stimulus device, and a pneumogastric nerve stimulus device, and various products have been launched and much research is being performed by medical equipment companies from various countries such as the U.S., Japan, and Europe.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention has been made in an effort to provide a nerve electrode having advantages of enhancing a rehabilitation effect by stimulating living body nerves and detecting a signal occurring from the nerves while suppressing inflammation generation for a long term within a living body. The present invention has been made in an effort to further provide a method of manufacturing the nerve electrode.

An exemplary embodiment of the present invention provides a nerve electrode that is inserted into a living body and that is configured to attach to nerves. The nerve electrode includes: i) a flexible substrate; ii) a plurality of electrodes that are separately positioned on the flexible substrate; and iii) an insulating layer that is positioned at a separation space of the plurality of electrodes and that insulates the plurality of electrodes. The plurality of electrodes include i) at least one linear electrode and ii) a planar electrode that is separated from the linear electrode. An anti-inflammatory drug transfer layer is positioned on the planar electrode.

The at least one linear electrode may include a separated plurality of linear electrodes, and the planar electrode may surround the linear electrode. The drug transfer layer may include nanofibers that are formed by electrospinning, and may include at least one drug that is selected from a group consisting of dexamethasone, sulindac, and tolmetin.

The nerve electrode may further include a hydrogel layer that is provided on the drug transfer layer, wherein the hydrogel layer may include at least one material that is selected from a group consisting of polyethylene glycol (PEG), aminoethyl methacrylated hyaluronic acid (HAAEMA), and gelatin hyaluronic acid (GelatinHA). The PEG layer may cover the linear electrode by directly contacting the linear electrode. The PEG layer may have an average thickness of 200 µm to 500 µm.

The nerve electrode may further include poly(3,4-ethylenedioxythiophene) (PEDOT) layer that is positioned on the linear electrode. The PEDOT layer may have an average thickness of 10 µm to 1000 µm. The nerve electrode may further include an electrode fixing layer that is positioned on the insulating layer and that covers an edge of at least one of the plurality of electrodes. The flexible substrate and the insulating layer may include polyimide.

Another embodiment of the present invention provides a method of manufacturing a nerve electrode that is inserted into a living body and that is configured to attach to nerves, the method including: i) providing a substrate; ii) providing a first polyimide layer on the substrate; iii) providing a first photoresist layer on the first polyimide layer; iv) partially exposing the first polyimide layer to the outside by partially removing the first photoresist layer; v) providing a plurality of electrodes that are separated by coating a conductive material on the partially exposed first polyimide layer; vi) exposing a first polyimide layer corresponding to a separation space between the plurality of electrodes to the outside by removing the first photoresist layer; vii) covering the plurality of electrodes by providing a second polyimide layer and covering the first polyimide layer corresponding to the separation space between the plurality of electrodes with the second polyimide layer; viii) providing a second photoresist layer on the second polyimide layer; ix) maintaining the second photoresist layer at a position corresponding to the separation space between the plurality of electrodes by partially removing the second photoresist layer; x) exposing the plurality of electrodes to the outside by etching the second polyimide layer and the second photoresist layer; and xi) providing a drug transfer layer on the exposed plurality of electrodes by electrospinning a solution in which anti-inflammatory drugs are contained. In the providing of a plurality of electrodes, the plurality of electrodes include i) a plurality of linear electrodes, and ii) a planar electrode enclosing the plurality of linear electrodes. In the providing of a drug transfer layer, the drug transfer layer is provided on the planar electrode.

The method may further include providing a hydrogel layer on the drug transfer layer, wherein the hydrogel layer may include at least one material that is selected from a group consisting of PEG, HAAEMA, and GelatinHA. The method may further include enabling the linear electrode and the PEDOT layer to directly contact by providing the PEDOT layer on the linear electrode. In the providing of a plurality of electrodes, the conductive material may include at least one metal that is selected from a group consisting of platinum and titanium.

In the maintaining of the second photoresist layer, the second photoresist layer may additionally remain at a position corresponding to an edge of the plurality of electrodes. In the providing of a drug transfer layer, the anti-inflammatory drugs may include at least one drug that is selected from a group consisting of dexamethasone, sulindac, and tolmetin. The method may further include removing the substrate.

Inflammation occurring due to insertion of a nerve electrode can be suppressed through a drug transfer layer. Further, because the drug transfer layer includes nanofibers that are made of a material having excellent biodegradability, the drug transfer layer does not harm a human body. Nanofibers are covered by a hydrogel layer, and by adjusting a thickness of the hydrogel layer, a quantity of drugs that are transferred to nerves can be easily adjusted.

DETAILED DESCRIPTION OF THE EMBODIMENTS

Figure 1:
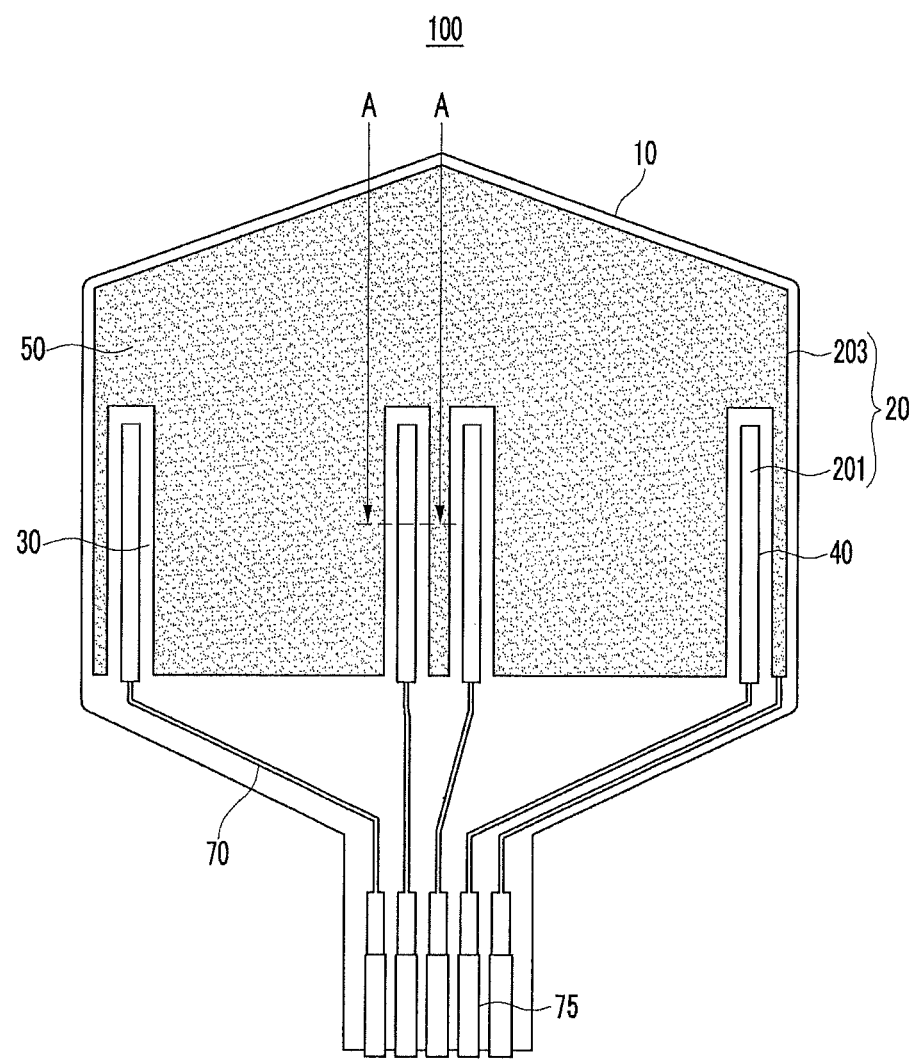
FIG. 1 is a top plan view illustrating a nerve electrode according to a first exemplary embodiment of the present invention.

When it is said that any part is positioned "on" another part, it means the part is directly on the other part or above the other part with at least one intermediate part. In contrast, if any part is said to be positioned "directly on" another part, it means that there is no intermediate part between the two parts.

Terms such as first, second, and third are used for describing various portions, components, areas, layers, and/or sections, but the terms are not limited thereto. The terms are used only for distinguishing any portion, component, area, layer, or section from other portions, components, areas, layers, or sections. Therefore, a first portion, component, area, layer, or section described hereinafter may be described as a second portion, component, area, layer, or section within the scope without deviating from the scope of the present invention.

Technical terms used here are to only describe a specific exemplary embodiment and are not intended to limit the present invention. Singular forms used here include plural forms unless explicitly described to the contrary. A meaning of "comprising" used in a specification embodies a specific characteristic, area, integer, step, operation, element, and/or component, and does not exclude presence or addition of another characteristic, area, integer, step, operation, element, and/or component.

Terms representing relative space of "lower" and "upper" may be used for more easily describing a relationship with another portion of a portion shown in the drawings. Such terms are intended to include other meanings or operations of an apparatus used together with a meaning that is intended in the drawings. For example, when an apparatus is inverted in the drawings, any portion described as disposed at a "lower" portion of other portions is described as being disposed at an "upper" portion of other portions. Therefore, the illustrative term "lower" includes both upper and lower directions. An apparatus may be rotated by 90° or another angle, and terms representing relative space are accordingly analyzed.

If not differently defined, all terms including technical terms and scientific terms used herein have the same meanings as those that may be generally understood by a person of common skill in the art. Terms defined in a generally used dictionary have meanings corresponding to a related technology document and presently disclosed contents, and are not to be construed as an idealized or very formal meaning unless stated otherwise.

An exemplary embodiment of the present invention described with reference to a cross-sectional view specifically illustrates an ideal exemplary embodiment of the present invention. As a result, various changes of explanatory diagrams, for example, changes of a manufacturing method and/or a specification, are expected. Therefore, an exemplary embodiment is not limited to a specific form of a shown area and may include, for example, form deformation by production. For example, an area shown or described as a flat area may have generally characteristics of rough or rough and nonlinear. Further, a portion shown as having a sharp angle may be round. Therefore, an area shown in the drawings is generally an approximate area, and a form thereof is not intended to illustrate an accurate form of an area and is not intended to narrow the scope of the present invention.

The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention.

FIG. 1 is a schematic top plan view illustrating a nerve electrode 100 according to a first exemplary embodiment of the present invention. A structure of the nerve electrode 100 of FIG. 1 only illustrates the present invention, and the present invention is not limited thereto. Therefore, a structure of the nerve electrode 100 may be changed to other forms.

The nerve electrode 100 that is shown in FIG. 1 is inserted into a living body and is applied to be attached to nerves. The nerve electrode 100 includes a flexible substrate 10, a plurality of electrodes 20, an insulating layer 30, an electrode fixing layer 40, and a drug transfer layer 50. Here, the plurality of electrodes 20 include linear electrodes 201 and a planar electrode 203. The planar electrode 203 is defined as an electrode having a larger surface area than that of the linear electrodes 201. The linear electrodes 201 and the planar electrode 203 are separated from each other, and the planar electrode 203 is positioned to surround the linear electrodes 201. The planar electrode 203 may be used for depositing nanofibers thereon, and the linear electrodes 201 may be used for stimulating nerves or detecting neural signals therefrom.

In addition, the nerve electrode 100 may further include other elements. For example, a nerve stimulus apparatus further includes a drawn-out line 70 and a drawn-out terminal 75. The nerve electrode 100 is inserted into a living body and is attached to nerves. The nerve electrode 100 includes the flexible substrate 10 that is applied to well attach it to nerves, and is formed using polyimide (PI).

Figure 2:
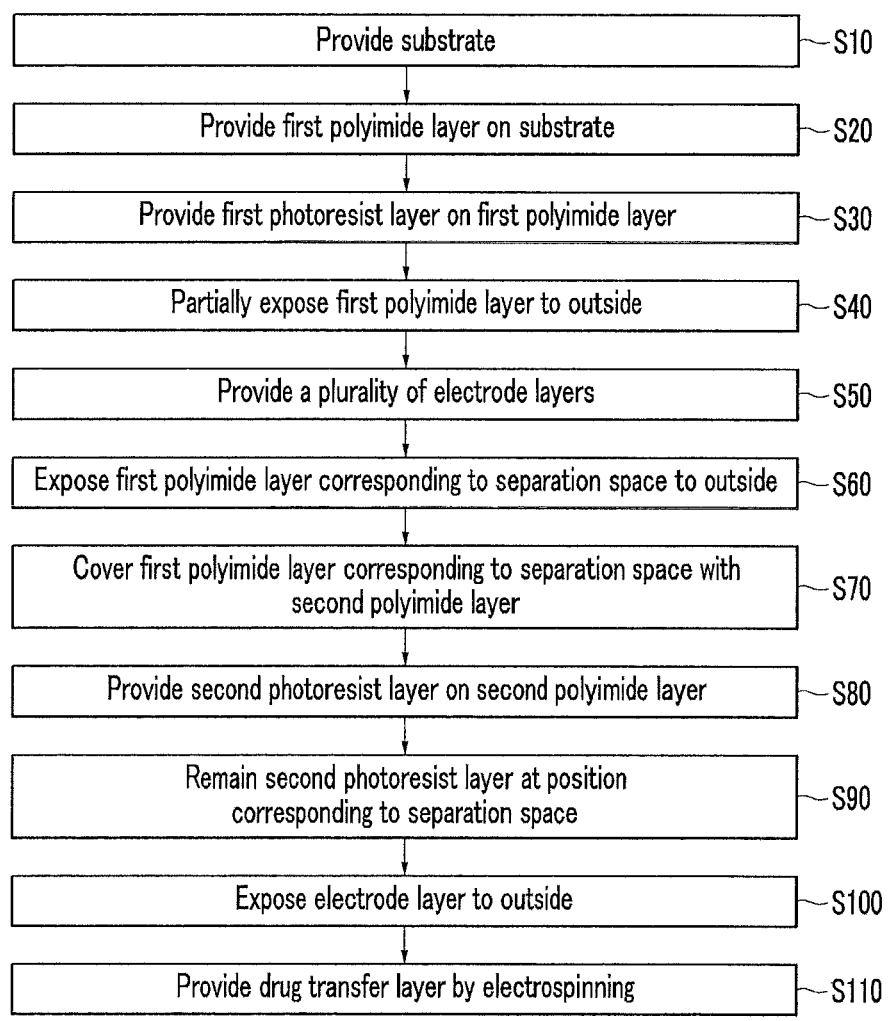
FIG. 2 is a flowchart illustrating a method of manufacturing the nerve electrode of FIG. 1.

FIG. 2 is a flowchart illustrating a process of manufacturing the nerve electrode 100 of FIG. 1, and FIGS. 3 to 13 are cross-sectional views illustrating each step of the process of manufacturing the nerve electrode 100 of FIG. 1. Hereinafter, a process of manufacturing a structure of a section AA of the nerve electrode 100 of FIG. 1 will be sequentially described with reference to FIGS. 2 and 3 to 13. A process of manufacturing the remaining portions of the nerve electrode 100, except for the foregoing portion, may easily understood by a person of common skill in the art and a detailed description thereof will be omitted.

As shown in FIG. 2, a method of manufacturing the nerve electrode 100 includes i) a step of providing a substrate (S10), ii) a step of providing a first polyimide layer on the substrate (S20), iii) a step of providing a first photoresist layer on the first polyimide layer (S30), iv) a step of partially exposing the first polyimide layer to the outside (S40), v) a step of providing a plurality of electrode layers (S50), vi) a step of exposing a first polyimide layer corresponding to a separation space to the outside (S60), vii) a step of covering the first polyimide layer corresponding to the separation space with a second polyimide layer (S70), viii) a step of providing a second photoresist layer on the second polyimide layer (S80), ix) a step of maintaining the second photoresist layer at a position corresponding to the separation space (S90), x) a step of exposing an electrode layer to the outside (S100), and xi) a step of providing a drug transfer layer on a plurality of electrodes that are exposed by electrospinning a solution in which anti-inflammatory drugs are contained (S120). In addition, although not shown in FIG. 2, a method of manufacturing the nerve electrode 100 may further include step of removing a substrate or a step of removing a mask layer. Further, a method of manufacturing of the nerve electrode 100 may further include other steps, as needed.

Figure 3:
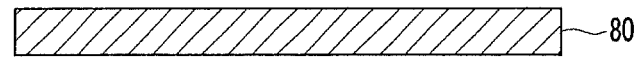
FIGS. 3 to 13 are cross-sectional views sequentially illustrating the method of manufacturing the nerve electrode of FIG. 2.

As shown in FIG. 2, at step S10, a substrate 80 is provided. For example, as shown in FIG. 3, the substrate 80 may use various materials such as a ceramic such as alumina, stainless use steel (SUS), silicon, a polymer, or aluminum foil.

Figure 4:
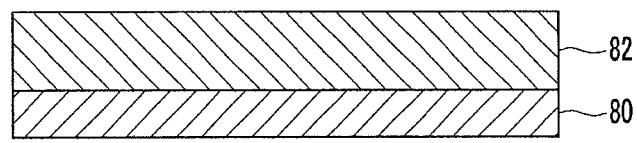

Next, at step S20 of FIG. 2, a first polyimide layer 82 is provided. That is, as shown in FIG. 4, the first polyimide layer 82 is formed in a stacked form on the substrate 80.

Figure 5:
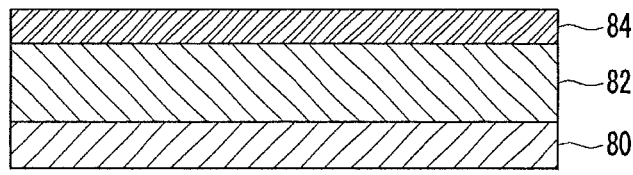

At step S30 of FIG. 2, a first photoresist layer 84 is provided. That is, as shown in FIG. 5, the first photoresist layer 84 is formed in a stacked form on the first polyimide layer 82.

Figure 6:
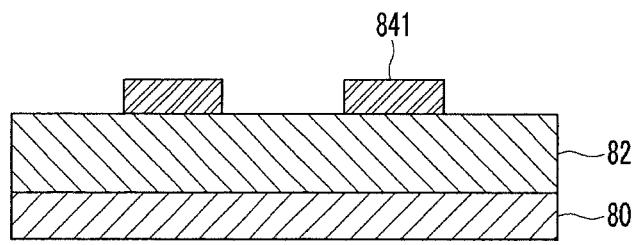

Next, at step S40 of FIG. 2, the first polyimide layer 82 is partially exposed to the outside. That is, as shown in FIG. 6, in order to partially expose the first polyimide layer 82 to the outside, by forming a photoresist layer 841 by etching and partially removing the first photoresist layer 84 (shown in FIG. 5) that is stacked on the first polyimide layer 82, the first polyimide layer 82 is partially exposed.

Figure 7:
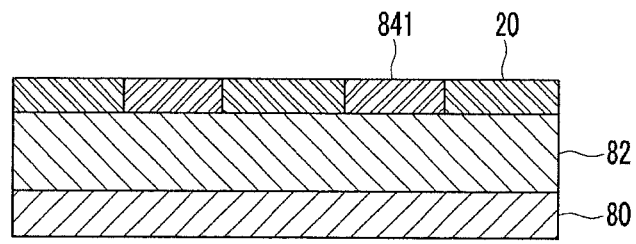

At step S50 of FIG. 2, the plurality of electrodes 20 are provided. That is, as shown in FIG. 7, the plurality of electrodes 20 are formed on a portion in which the first polyimide layer 82 is exposed. Here, the electrodes 20 may be made of a conductive material. For example, the conductive material may be at least one metal that is selected from a group consisting of platinum and titanium.

Figure 8:
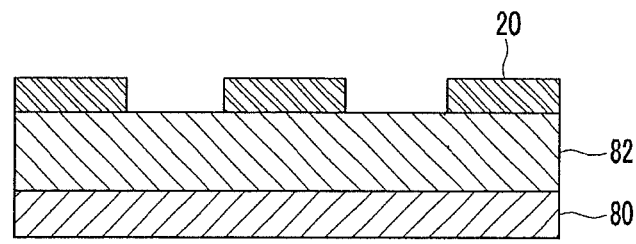

Next, at step S60 of FIG. 2, the first polyimide layer 82 is exposed to the outside. That is, as shown in FIG. 8, by etching and removing the photoresist layer 841 corresponding to a separation space of the electrodes 20, the first polyimide layer 82 is again exposed to the outside.

Figure 9:
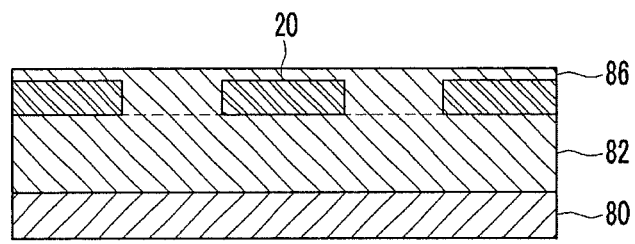

At step S70 of FIG. 2, a second polyimide layer 86 is provided. That is, as shown in FIG. 9, the electrodes 20 that are formed on the first polyimide layer 82 and the first polyimide layer 82 corresponding to separation space thereof are covered with the second polyimide layer 86. For example, the second polyimide layer 86 is formed using a spin coating method.

Figure 10:
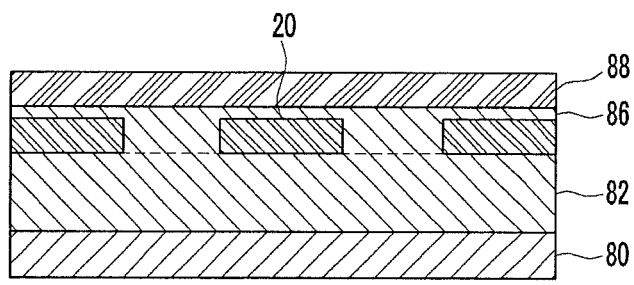

Next, at step S80 of FIG. 2, a second photoresist layer 88 is provided. That is, as shown in FIG. 10, the second photoresist layer 88 is formed in a stacked form on the second polyimide layer 86.

Figure 11:
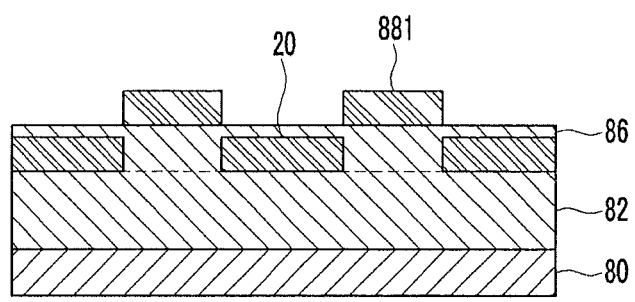

At step S90 of FIG. 2, the second photoresist layer 88 is remained. That is, as shown in FIG. 11, in order to expose the second polyimide layer 86 corresponding to the separation space to the outside, the second photoresist layer 88 is etched and partially removed. By remaining the second photoresist layer 88, a second photoresist layer 881 is formed, and the second polyimide layer 86 is partially exposed.

Figure 12:
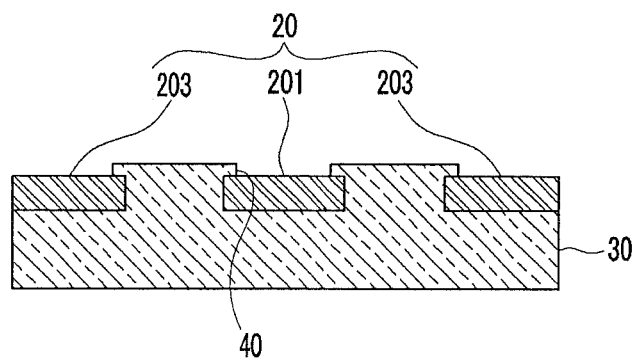
Figure 13:
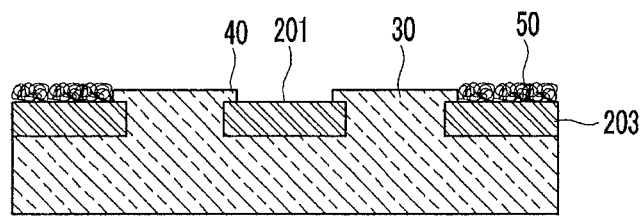

Next, at step S100 of FIG. 2, the electrodes 20 are exposed to the outside. That is, as shown in FIG. 12, in order to expose the electrodes 20 to the outside, the partially exposed second polyimide layer 86 (shown in FIG. 11) is etched through step S90 of FIG. 2, and by etching the remaining second photoresist layer 881 (shown in FIG. 11), the electrodes 20 are exposed to the outside. Here, the unetched first polyimide layer 82 (shown in FIG. 11) and the second polyimide layer 86 are positioned at the separation space of the plurality of electrodes 20 while forming the flexible substrate 10 of the nerve electrode 100, thereby forming the insulating layer 30 for insulating the plurality of electrodes 20. The plurality of electrodes 20 include the linear electrodes 201 and the planar electrode 203. The first polyimide layer 82 and the second polyimide layer 86 are formed as the electrode fixing layer 40 that covers an edge of the electrodes 20. The substrate 80 (shown in FIG. 11) may be separated from the flexible substrate 10. The substrate 80 may be removed with a method of separating by grasping. The substrate 80 may be reused after being separated.

At step 110 of FIG. 2, the drug transfer layer 50 is provided on a plurality of electrodes that are exposed by electrospinning a solution in which anti-inflammatory drugs are contained. An electrospinning process may be easily understood by a person of common skill in the art and therefore a detailed description thereof will be omitted. For example, for electrospinning, a mask layer is provided on the rest of portion except the planar electrode 203 of FIG. 13. When a voltage is applied to the planar electrode 203 and electrospinning anti-inflammatory drugs, the drug transfer layer 50 is attached to and formed on the planar electrode 203. Therefore, because the drug transfer layer 50 having a wide area may be formed, inflammation occurring when attaching the nerve electrode 100 (shown in FIG. 1) to a living body can be suppressed.

Because the drug transfer layer 50 is stacked and formed using electrospinning, the thickness of the drug transfer layer 50 can be adjusted. When electrospinning, a suspension containing anti-inflammatory drugs is filled into a syringe pump and is slowly ejected in a constant speed. In this way, an ejected suspension is electrospun.

In an electrospinning processing process, a sol-gel reaction is performed due to solvent evaporation at the inside of the suspension. As a result, the drug transfer layer 50 is formed with nanofibers in which drugs are evenly distributed. Because nanofibers are slowly dissolved within a living body for 6 months to 1 year, drugs can be slowly and efficiency transferred.

The drug transfer layer 50 includes a plurality of nanofibers. Because nanofibers are formed for discharging drugs containing antibiotics, a phenomenon that inflammation occurs in nerves can be prevented. As antibiotics, dexamethasone, sulindac, or tolmetin may be used. By removing the used mask layer, the nerve electrode 100 (shown in FIG. 1) is manufactured.

Figure 14:
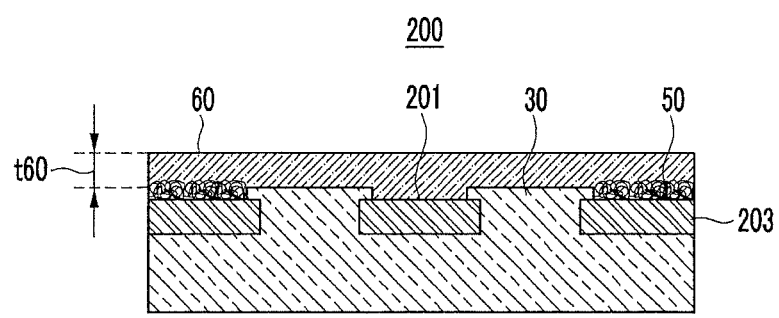
FIGS. 14 and 15 are cross-sectional views illustrating a nerve electrode according to second and third exemplary embodiments of the present invention.

FIG. 14 illustrates a section structure of a nerve electrode 200 according to a second exemplary embodiment of the present invention. As shown in FIG. 14, a hydrogel layer 60 is formed on a drug transfer layer 50. The hydrogel layer 60 directly contacts a linear electrode 201. The hydrogel layer 60 is formed by spin coating.

Here, an average thickness t60 of the hydrogel layer 60 may be 200 μm to 500 μm. If an average thickness of the hydrogel layer 60 is excessively small, all electrospun nanofibers cannot be coated. Further, if an average thickness of the hydrogel layer 60 is excessively large, an initial discharging amount of drugs that are loaded in nanofibers is very small and thus inflammation may occur. Therefore, an average thickness of the hydrogel layer 60 is adjusted to the above-described range.

The hydrogel layer 60 is coated on the drug transfer layer 50, and a release speed of drugs is adjusted according to a thickness thereof. Therefore, when the hydrogel layer 60 has a small thickness, drugs are quickly emitted. In contrast, when the hydrogel layer 60 has a large thickness, drugs are slowly discharged. The hydrogel layer 60 is made of a material such as polyethylene glycol (PEG), aminoethyl methacrylated hyaluronic acid (HAAEMA), or gelatin hyaluronic acid (GelatinHA).

Figure 15:
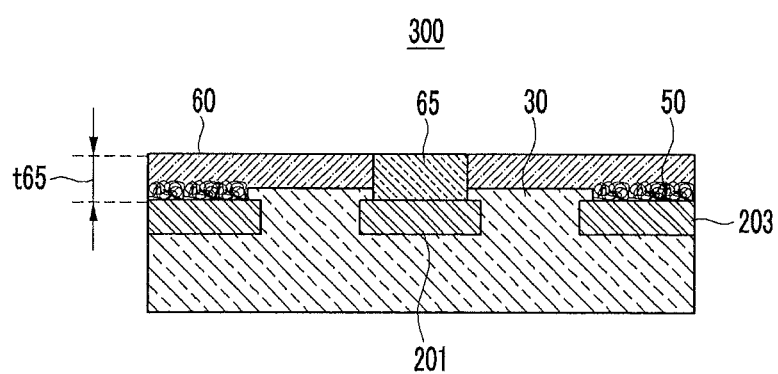

FIG. 15 illustrates a section structure of a nerve electrode 300 according to a third exemplary embodiment of the present invention. As shown in FIG. 15, a poly(3,4-ethylenedioxythiophene) (PEDOT) layer 65 is formed on a linear electrode 201. Here, an average thickness t65 of the PEDOT layer 65 may be 10 μm to 1000 μm. By adjusting an average thickness t65 of the PEDOT layer 65 to the above-described range, inflammation is efficiently suppressed. A thickness of the PEDOT layer 65 is determined by a thickness of the previously formed hydrogel layer 60. By boring a hydrogel layer 60 that is formed on a linear electrode 201, the PEDOT layer 65 directly contacts the linear electrode 201.

EXPERIMENTAL EXAMPLES

Hereinafter, the present invention will be described in detail through Experimental Examples. Such Experimental Examples only illustrate the present invention, and the present invention is not limited thereto.

A nerve electrode was produced with the same method as that shown in FIG. 2. An effect of the nerve electrode was determined through an in vitro experiment.

Figure 16:
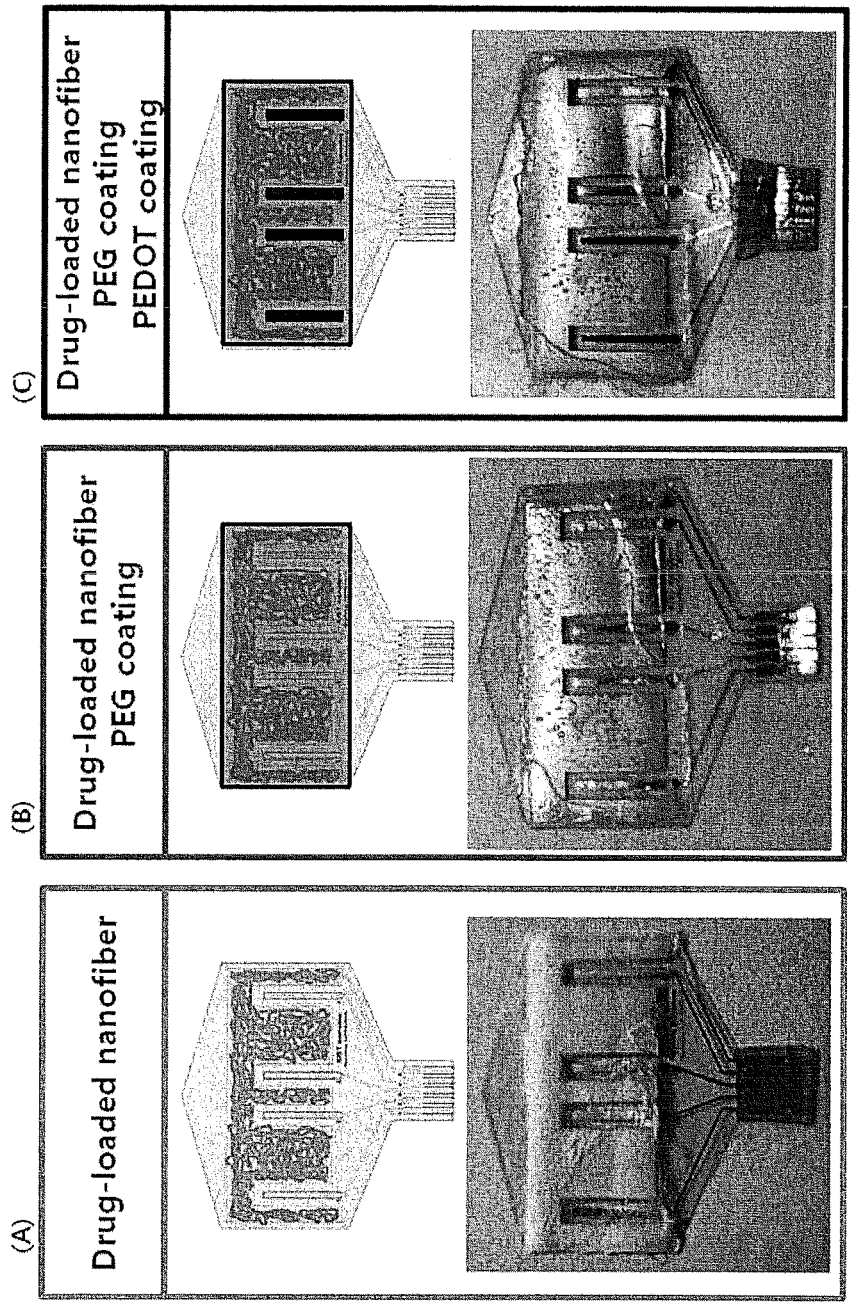
FIG. 16 A to C are photographs of nerve electrodes that are produced according to Experimental Examples 1 to 3 of the present invention.

FIG. 16 is a photograph illustrating a nerve electrode that is produced according to Experimental Examples 1 to 3 of the present invention. That is, (A) of FIG. 16 illustrates a nerve electrode that is produced according to Experimental Example 1 in which nanofibers including drugs are stacked, (B) of FIG. 16 illustrates a nerve electrode that is produced according to Experimental Example 2 that is stacked with nanofibers including drugs and that is coated with PEG, and (C) of FIG. 16 illustrates a nerve electrode that is produced according to Experimental Example 3 that is stacked with nanofibers including drugs and that is coated with PEG and PEDOT.

A drug release profile using nerve electrodes that are produced according to Experimental Examples 1 to 3 of the present invention was sequentially analyzed and an effect thereof was determined.

Drug Release Experiment and Result

Figure 17:
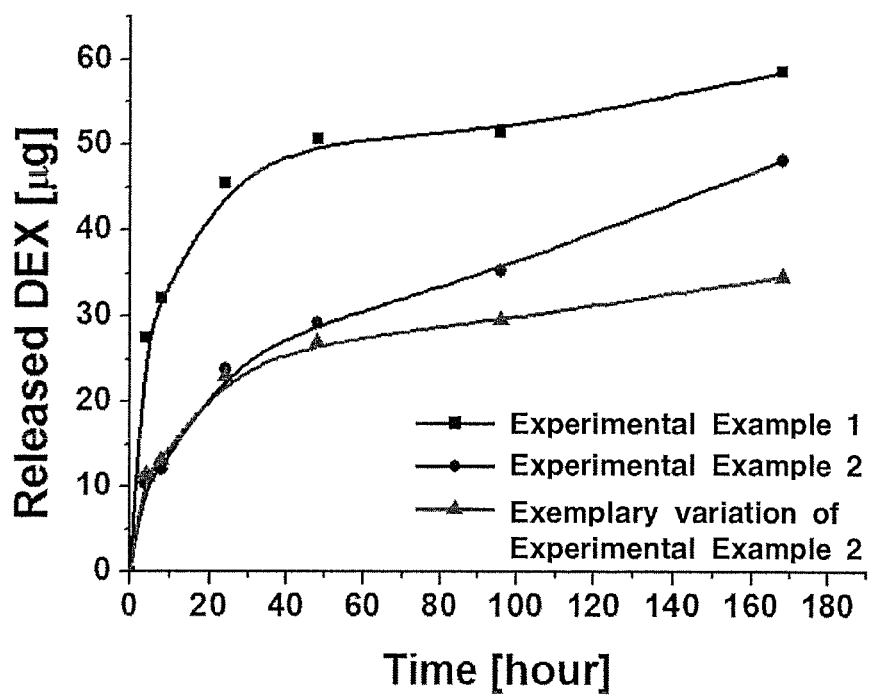
FIG. 17 is a graph illustrating an analysis result of a drug release profile of a nerve electrode according to Experimental Example 1, Experimental Example 2, and an exemplary variation of Experimental Example 2.

FIG. 17 illustrates an analysis result of a drug release profile using high performance liquid chromatography (HPLC). That is, FIG. 17 illustrates a sequential analysis result of a drug release profile of dexamethasone using nerve electrodes of Experimental Examples 1 and 2 that are produced according to an exemplary embodiment of the present invention, and a nerve electrode according to an exemplary variation of Experimental Example 2.

The nerve electrode of Experimental Example 2 was produced by changing the thickness of PEG, and a drug release difference according to PEG thickness was also analyzed. The thickness of PEG was formed so that thin PEG is 200 nm and thick PEG is 450 nm to 500 nm. As an analysis result, it was observed that a nerve electrode according to an exemplary variation of Experimental Example 2 is slower and more constant in drug release speed than the nerve electrode of Experimental Example 2.

Electrochemical Impedance Experiment and Result

Electrochemical impedance was analyzed using nerve electrodes that were produced according to Experimental Examples 2 and 3 of the present invention, and an effect thereof was determined.

Figure 18:
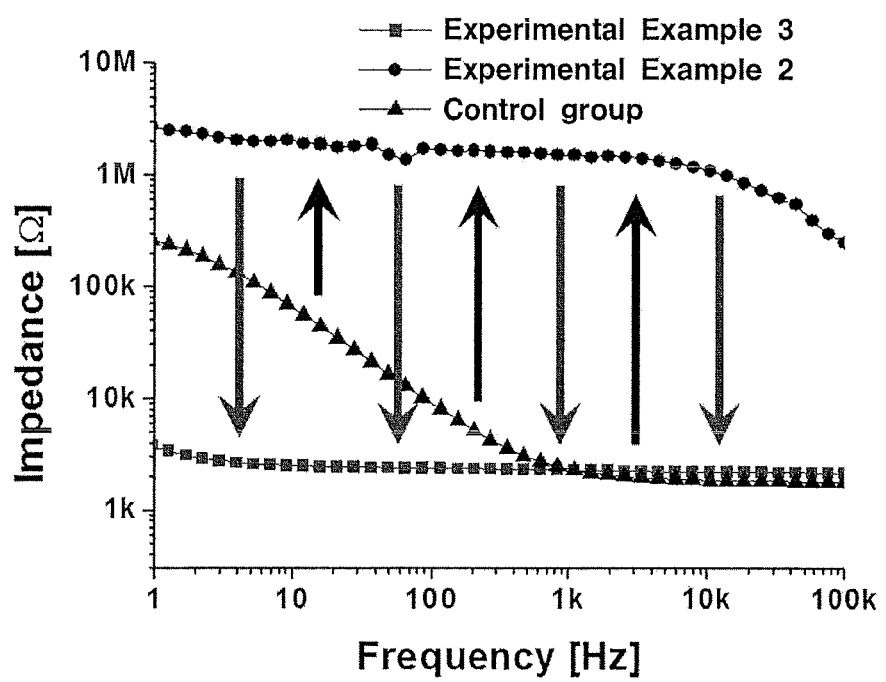
FIG. 18 is a graph illustrating an analysis result of electrochemical impedance of a nerve electrode according to a control group, Experimental Example 2, and Experimental Example 3.

FIG. 18 illustrates an analysis result of electrochemical impedance. That is, FIG. 18 illustrates an analysis result of electrochemical impedance using nerve electrodes that were produced according to Experimental Examples 2 and 3 of the present invention.

As an impedance analysis result, in a nerve electrode of a control group, when a frequency thereof rises, impedance drops, but it was observed that nerve electrodes that are produced according to Experimental Examples 2 and 3 of the present invention maintain a relatively constant value. Further, it was observed that the nerve electrode has a lower resistance value.

Cyclic Voltammetry Experiment and Result

Cyclic voltammetry was analyzed using the nerve electrodes that are produced according to Experimental Examples 2 and 3 of the present invention, and an effect thereof was determined.

Figure 19:
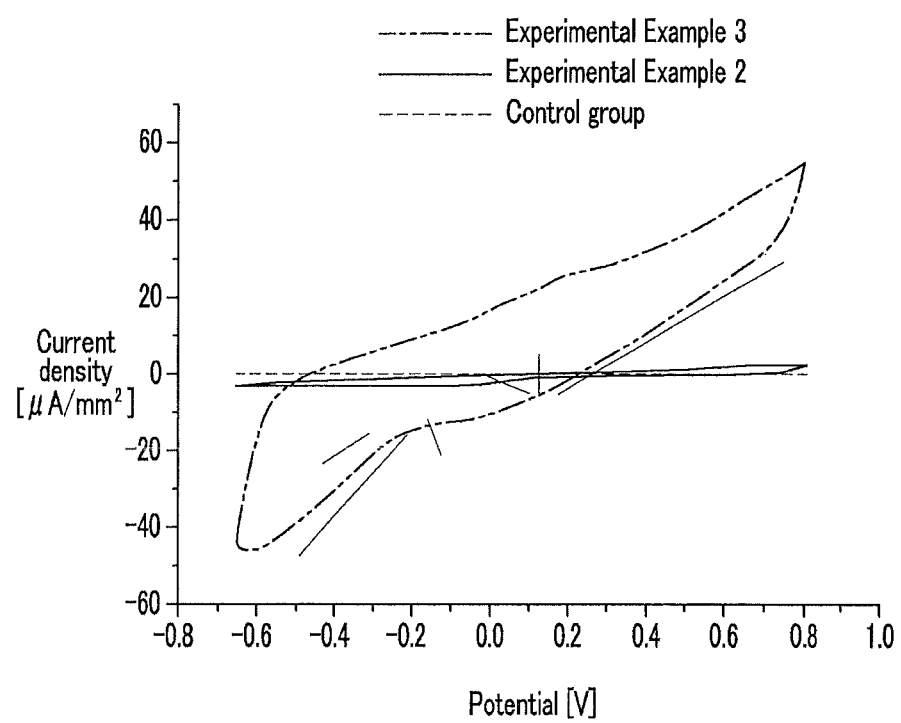
FIG. 19 is a graph illustrating an analysis result of cyclic voltammetry of nerve electrodes according to a control group, Experimental Example 2, and Experimental Example 3.

FIG. 19 illustrates an analysis result of cyclic voltammetry. That is, FIG. 19 illustrates an analysis result of cyclic voltammetry using the nerve electrodes that are produced according to Experimental Examples 2 and 3 of the present invention.

As a CV analysis result, it was observed that the nerve electrodes that are produced according to Experimental Examples 2 and 3 of the present invention represent a constant current density and there is no difference in an active area of a CV result. However, it was observed that a control group represents a larger active area than the nerve electrodes that are produced according to Experimental Examples 2 and 3 of the present invention according to a change of a potential value.

Anti-inflammation and Biocompatibility Experiment and Result

Improvement of anti-inflammation and biocompatibility through surface coating of a nerve electrode was determined.

Figure 20:
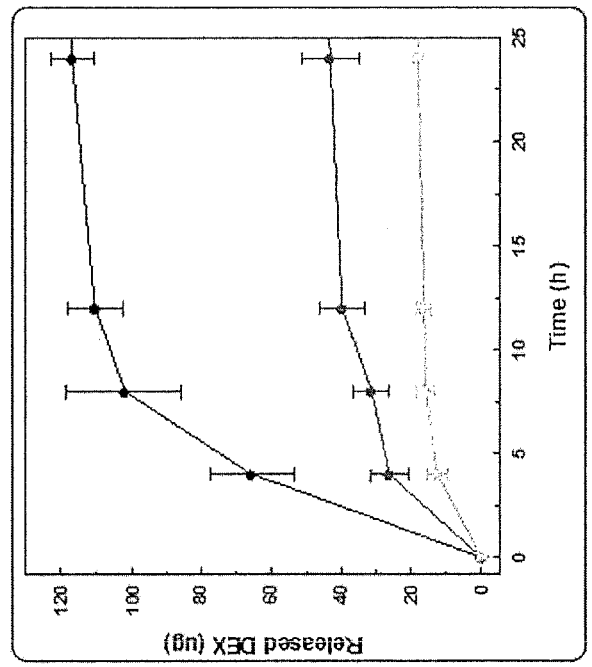
FIG. 20 illustrates a determination result of drug loading efficiency increase of a nerve electrode according to Experimental Example 1 of the present invention.
Figure 20:
Figure 20:
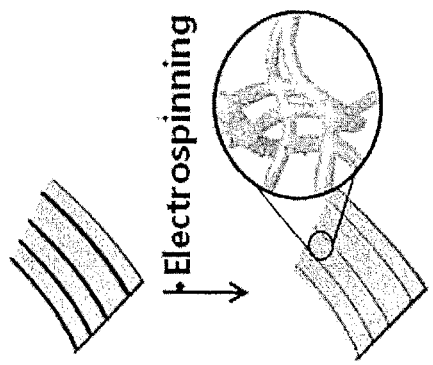
Figure 21:
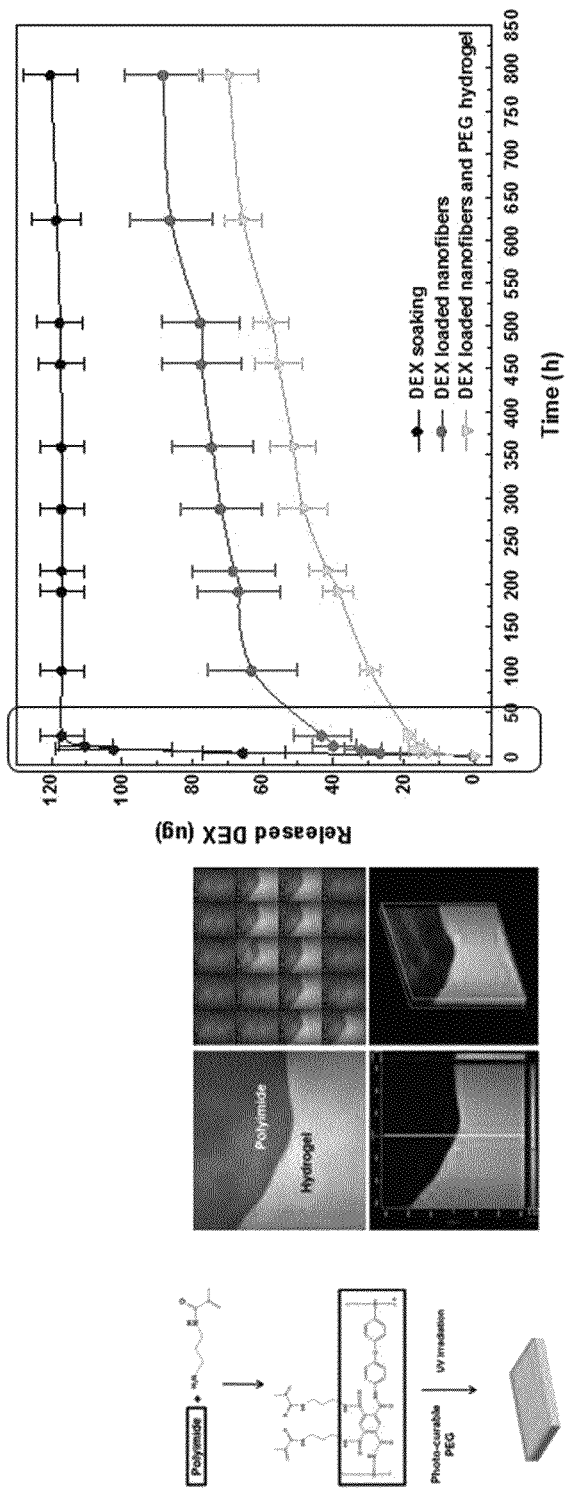
FIG. 21 illustrates a determination result of a PEG layer forming effect of a nerve electrode according to Experimental Example 2 of the present invention.
Figure 22:
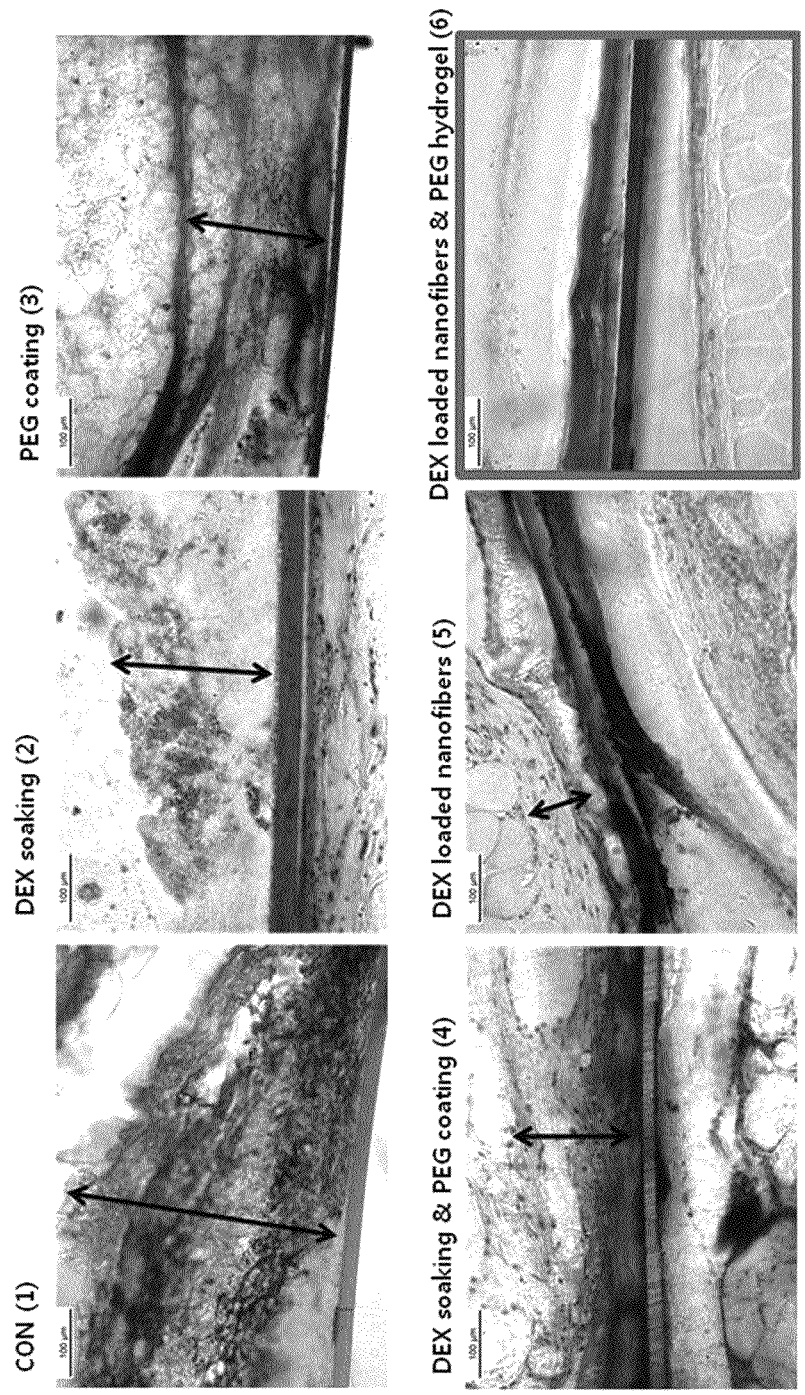
FIG. 22 is a photograph illustrating a tissue test result according to a surface coating difference of a nerve electrode.

FIG. 20 illustrates a result in which drug-loaded nanofibers are selectively applied at a platinum surface of a nerve electrode and illustrates a determination result of drug loading efficiency increase, and FIG. 21 illustrates a determination result of an effect in which PEG hydrogel is coating at a nerve electrode. FIG. 22 is a photograph illustrating a tissue test result according to a surface coating difference of a nerve electrode.

As shown in FIG. 20, when drug-loaded nanofibers were selectively applied at a platinum surface of a nerve electrode through electrospinning, it was observed that the nerve electrode to which drugs loading type nanofibers were selectively applied was slower and more constant in drug release speed than a nerve electrode to which drug-loaded nanofibers are not selectively applied.

Next, as shown in FIG. 21, it was observed that generation of scar and fibrous tissue was suppressed through coating of PEG hydrogel to the nerve electrode, and this result showed a determination result of a buffing operation between the nerve electrode and a tissue. Further, a sequential analysis result of a drug release profile of a nerve electrode (black circle) that is produced by soaking in dexamethasone, a nerve electrode (red circle) that is stacked with nanofibers including drugs, and a nerve electrode (green inverted triangle) that is stacked with nanofibers including drugs and that is coated with PEG hydrogel was represented with a graph. As analysis results, it was observed that the drug release speed of the nerve electrode that is stacked with nanofibers including drugs and that is coated with PEG hydrogel is slow and constant.

As shown in FIG. 22, an inflammation level according to a surface coating difference of a nerve electrode of one comparison group and nerve electrodes of five control groups (a dexamethasone soaking nerve electrode, a PEG coating nerve electrode, a PEG coating nerve electrode after being soaked in dexamethasone, a nerve electrode that is stacked with nanofibers including dexamethasone drugs, and a nerve electrode that is stacked with nanofibers including dexamethasone drugs and that is coated with PEG hydrogel) was observed through a tissue test of a subcutaneous tissue portion of a beagle at one week after current stimulus. As an observed result, in the nerve electrode that is stacked with nanofibers including dexamethasone drugs and that is coated with PEG hydrogel, a result in which an inflammation reaction scarcely existed was observed.

COMPARATIVE EXAMPLE

A nerve cuff electrode was prepared. In order to determine an effect of the nerve electrode, a beagle was selected as an animal model, and the nerve electrode was implanted to sciatic nerves and an effect thereof was determined.

Figure 23:
FIG. 23 is a photograph illustrating a state in which a nerve electrode having no drug is implanted to a beagle.
Figure 24:
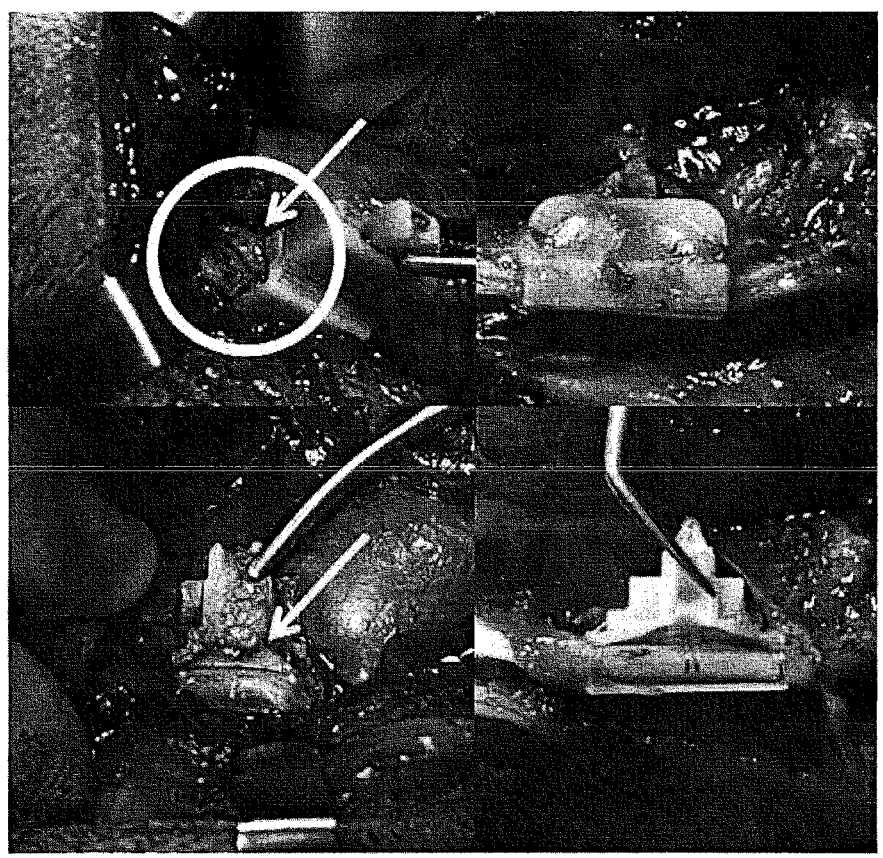
FIGS. 24 and 25 are photographs illustrating the inside and outside of a living body in which a nerve electrode having no drug is implanted to a beagle's nerves for two months.
Figure 25:
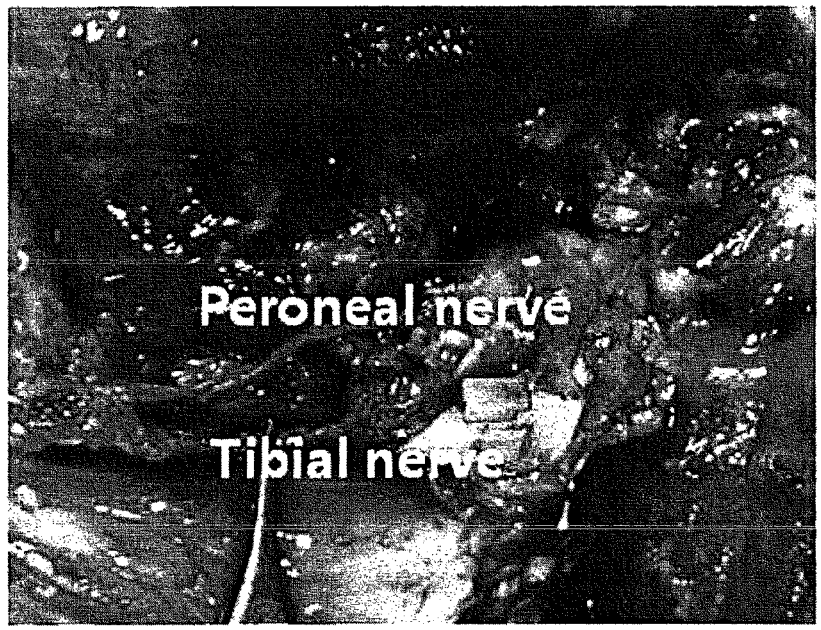
Figure 25:

FIG. 23 is a photograph illustrating a state in which a nerve electrode having no drug is implanted to a beagle, and FIGS. 24 and 25 are photographs illustrating a living body in which a nerve electrode having no drug is implanted to a beagle. When the nerve electrode is implanted to the beagle, the electrode was connected to all three portions of sciatic nerves, peroneal nerves, and tibial nerves.

Comparative Example 1

The nerve cuff electrode was implanted to the sciatic nerves of a leg portion under a pelvis of the beagle, a current stimulus was applied to the sciatic nerves and the peroneal nerves in an anesthetized state, and an output signal was determined.

Experiment Result of Comparative Example 1

Figure 26:
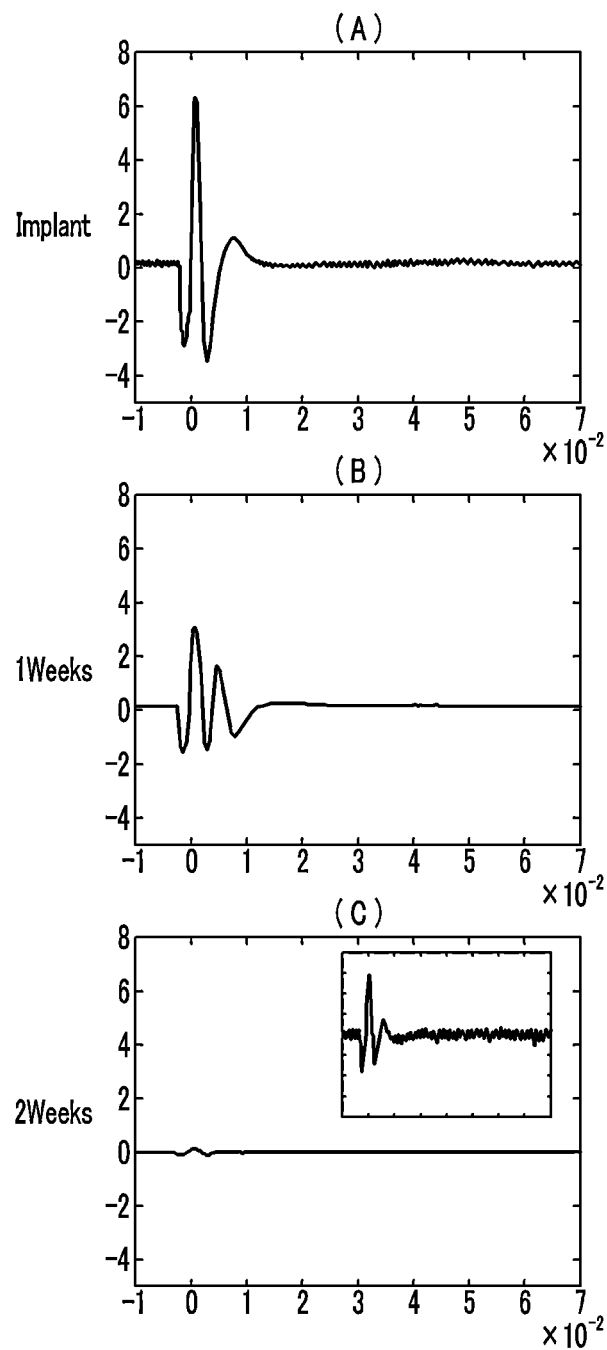
FIGS. 26A to 26C are graphs illustrating a living body reaction according to a nerve electrode operation of immediately after, 1 week after, and 2 weeks after implant of a nerve electrode in which drugs are not loaded according to Comparative Example 1.

FIG. 25 is a photograph illustrating a leg portion of the beagle of Comparative Example 1, and FIG. 26 is a graph illustrating a living body reaction according to operation of a nerve electrode at 1 week and 2 weeks after a nerve electrode having no drug is implanted according to Comparative Example 1.

As shown in FIG. 26, as a result in which a current stimulus is applied with a pulse of 250 uS and 400 uA, at 2 weeks after implant of the nerve cuff electrode, it was observed that an output signal disappears and stimulus does not exist. It was expected that this was caused by inflammation due to a current stimulus. Therefore, in order to maintain an output signal, it could be seen that it is necessary to remove inflammation.

Comparative Example 2

By observing sciatic nerve and tibial nerve section tissues of the beagle, an influence of a current stimulus was determined.

Experiment Result of Comparative Example 2

Figure 27:
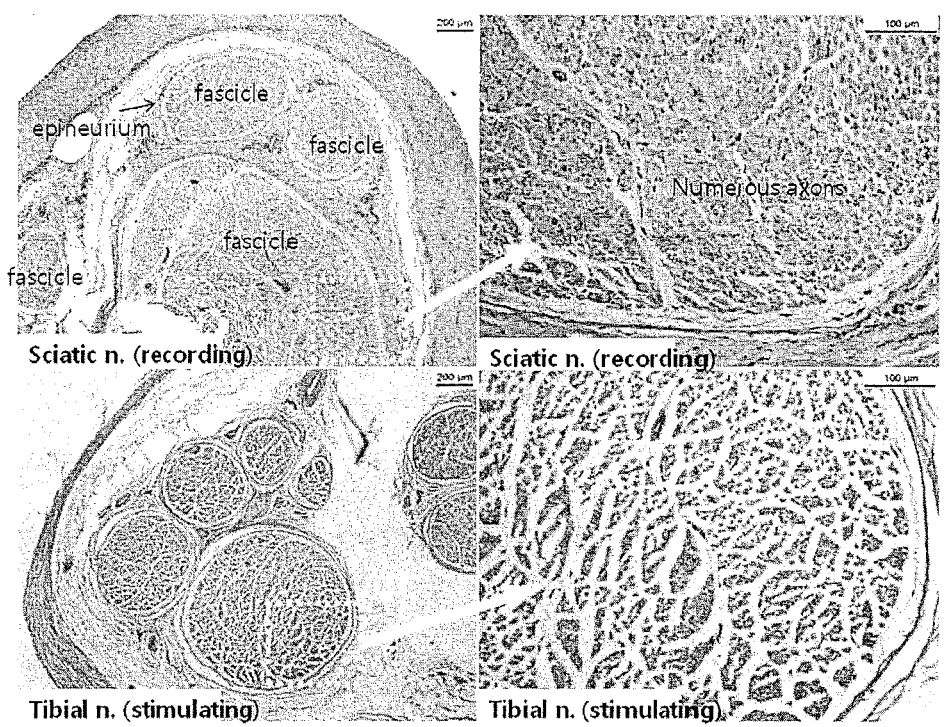
FIG. 27 is a photograph illustrating a section of sciatic nerves and tibial nerves of a beagle that receives a current stimulus according to Comparative Example 2.

FIG. 27 is a photograph illustrating a section of sciatic nerves and tibial nerves of the beagle due to a current stimulus that is performed according to Comparative Example 2. As shown in FIG. 27, as a result of an influence of a current stimulus through a section of sciatic nerves and tibial nerves of the beagle, an internal cell of stimulated tibial nerves is stimulated and thus inflammation is generated, and necrosis of some cells was thus observed. In sciatic nerves corresponding to output and record portions of a signal, epineurium and fascicle are not damaged in a section of a nerve cell, and thus it was observed that when some nerve bundles are enlarged, many numerous axons are maintained. However, in tibial nerves corresponding to an input unit of a current stimulus, it was observed that due to damage of epineurium, inflammation has occurred, and it was observed that when some nerve bundles are enlarged, numerous axons are damaged.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A nerve electrode that is insertable into a living body, the nerve electrode comprising:
   a flexible substrate;
   an insulating layer on the flexible substrate;
   a plurality of substantially co-planar electrodes that are separately positioned on the insulating layer and spaced from each other, wherein the plurality of electrodes includes a planar electrode and a plurality of continuous linear electrodes,
wherein the planar electrode includes a central axis extending from a first end to a second end,
wherein the second end includes a plurality of elongated openings parallel to the axis, with at least one of the openings adjacent the axis,
wherein one of the plurality of openings of the planar electrode substantially surrounds a corresponding one of the plurality of linear electrodes,
wherein each of the linear electrodes is parallel to the axis and has a first end within the opening and a second, opposite end extending outside the opening,
wherein the insulating layer extends between the planar electrode and each of the plurality of linear electrodes and insulates the plurality of electrodes from each other,
wherein each of the plurality of linear electrodes has an area, and the planar electrode has an area that is larger than the area of any of the plurality of linear electrodes,
wherein an anti-inflammatory drug transfer layer is positioned on the planar electrode, and
wherein the drug transfer layer is made of nanofibers; and a hydrogel layer extending over the nanofibers,
wherein the second end of the planar electrode and the extending second ends of the linear electrodes are connected to leads.

2. The nerve electrode of claim 1, wherein the drug transfer layer comprises at least one drug that is selected from the group consisting of dexamethasone, sulindac, and tolmetin incorporated on the nanofibers.

3. The nerve electrode of claim 2,
wherein the hydrogel layer includes at least one material that is selected from the group consisting of polyethylene glycol, aminoethyl methacrylated hyaluronic acid, and gelatin hyaluronic acid.

4. The nerve electrode of claim 3 further comprising a poly(3,4-ethylenedioxythiophene) layer that is positioned on the plurality of linear electrodes.

5. The nerve electrode of claim 4, wherein the poly(3,4-ethylenedioxythiophene) layer has an average thickness of 10 μm to 1000 μm.

6. The nerve electrode of claim 3, wherein the hydrogel layer includes the polyethylene glycol and covers each of the plurality of linear electrodes by directly contacting each of the plurality of linear electrodes.

7. The nerve electrode of claim 3, wherein the hydrogel layer includes the polyethylene glycol and has an average thickness of 200 μm to 500 μm.

8. The nerve electrode of claim 1 further comprising an electrode fixing layer that is positioned on the insulating layer and that covers an edge of at least one of the plurality of electrodes.

9. The nerve electrode of claim 1, wherein the flexible substrate and the insulating layer comprise polyimide.

* * * * *